US00PP29570P3

(12) United States Plant Patent
Uchneat

(10) Patent No.: US PP29,570 P3
(45) Date of Patent: Jul. 31, 2018

(54) ***SALVIA* PLANT NAMED 'SGRRE04-1'**

(50) Latin Name: *Salvia splendens*
Varietal Denomination: SGRRE04-1

(71) Applicant: Michael Uchneat, Bellefonte, PA (US)

(72) Inventor: Michael Uchneat, Bellefonte, PA (US)

(73) Assignee: Garden Genetics, LLC, Bellefonte, PA (US)

( * ) Notice: Subject to any disclaimer, the term of this patent is extended or adjusted under 35 U.S.C. 154(b) by 0 days.

(21) Appl. No.: 15/530,306

(22) Filed: Dec. 21, 2016

(65) Prior Publication Data

US 2018/0177104 P1 Jun. 21, 2018

(51) Int. Cl.
*A01H 5/02* (2018.01)

(52) U.S. Cl.
USPC ..... Plt./475

(58) Field of Classification Search
USPC ..... Plt./475
See application file for complete search history.

*Primary Examiner* — Susan McCormick Ewoldt
(74) *Attorney, Agent, or Firm* — Cassandra Bright

(57) ABSTRACT

A new and distinct *Salvia* cultivar named 'SGRRE04-1' is disclosed, characterized by vigorous plants with a large, upright form and long flowering period. Flowers are bright red. Calyces are persistent and retain their red color. The new variety is a *Salvia splendens*, normally produced as an outdoor garden or container plant.

2 Drawing Sheets

Figure 1:
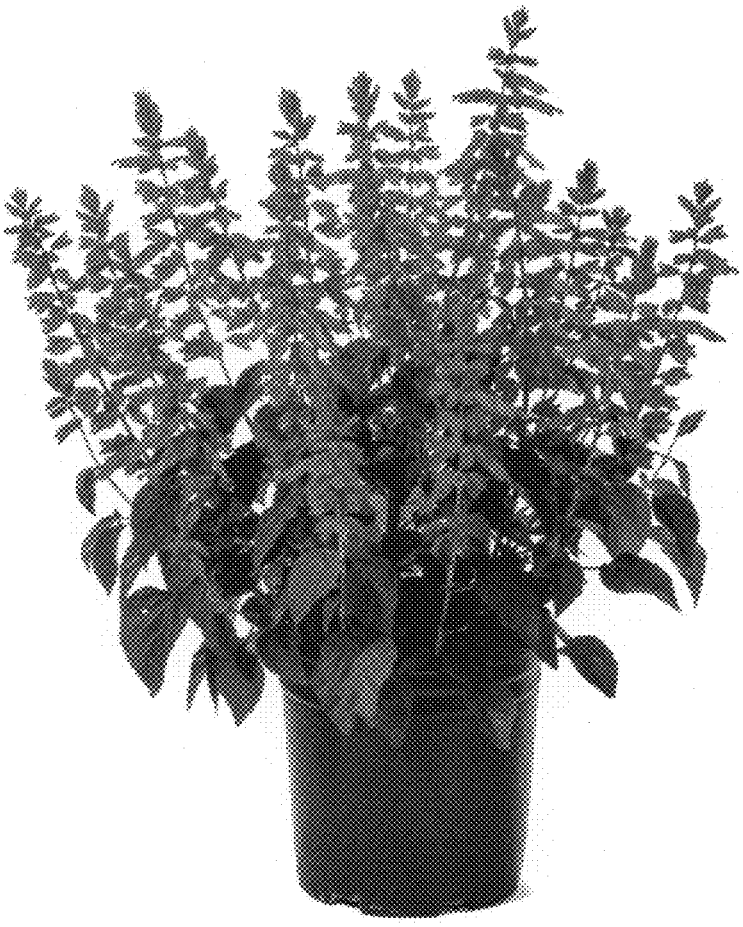

Latin name of the genus and species: *Salvia splendens*.
Variety denomination: 'SGRRE04-1'.

BACKGROUND OF THE INVENTION

The new *Salvia* cultivar is a product of a planned breeding program conducted by the inventor, Michael Uchneat in Bellefonte, Pa. The objective of the breeding program was to produce new *Salvia splendens* varieties with large, upright plant habits in a range of flower colors and persistent calyces. The self-pollination resulting in this new variety was made during June of 2013.

The parent variety is an unpatented, proprietary, *Salvia splendens* referred to as '28744-1'. This parent variety was self-pollinated and the resulting seed collected. Seed collected from this self-pollination was grown out, with the result of a variety of flower colors and plant sizes observed among the seedling population. The new variety was identified as a potentially interesting selection, from this seedling population in August 2014, at a greenhouse in Bellefonte, Pa.

Asexual reproduction of the new cultivar 'SGRRE04-1' by vegetative cuttings was first performed during August of 2014, at a research greenhouse in Bellefonte, Pa. Subsequent propagation has shown that the unique features of this cultivar are stable and reproduced true to type on successive generations.

SUMMARY OF THE INVENTION

The cultivar 'SGRRE04-1' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SGRRE04-1' These characteristics in combination distinguish 'SGRRE04-1' as a new and distinct *Salvia* cultivar:

1. Vigorous, large, upright plant larger than most *Salvia splendens* in the trade.
2. Long flowering period from young plant until frost.
3. Calyces are persistent and color of the calyx is retained.
4. Bright red flowers.

PARENT COMPARISON

Plants of the new cultivar 'SGRRE04-1' are similar to plants of the parent in most horticultural characteristics, however, plants of the new cultivar 'SGRRE04-1' differ in the following:

1. The parent variety has a more tightly packed inflorescence, with less space between individual flowers than the new variety.
2. Size of the new variety is approximately 25% to 30% larger in size of than the parent variety.

COMMERCIAL COMPARISON

Plants of the new cultivar 'SGRRE04-1' can also be compared to the commercial variety *Salvia splendens* 'Saucy Red', unpatented. These varieties are similar in most horticultural characteristics; however 'SGRRE04-1' differs in the following:

1. The new variety has brighter red flowers than 'Saucy Red'.
2. A higher percentage of calyx persistence is observed in the new variety.
3. Foliage of the new variety is darker green.
4. The new variety is not sterile, whereas 'Saucy Red' appears to be sterile.

Plants of the new cultivar 'SGRRE04-1' can also be compared to the commercial variety *Salvia splendens*

'Lighthouse Red', unpatented. These varieties are similar in most horticultural characteristics; however 'SGRRE04-1' differs in the following:

1. Flowers of the new variety do not fade as quickly as flowers of 'Lighthouse Red'.
2. Flowering spikes of the new variety are longer than those of 'Lighthouse Red'.

BRIEF DESCRIPTION OF THE PHOTOGRAPHS

The accompanying photograph in FIG. 1 illustrates in full color a typical plant of 'SGRRE04-1' grown in a greenhouse, in Santa Paula, Calif., in a commercial 10 inch container.

Figure 2:
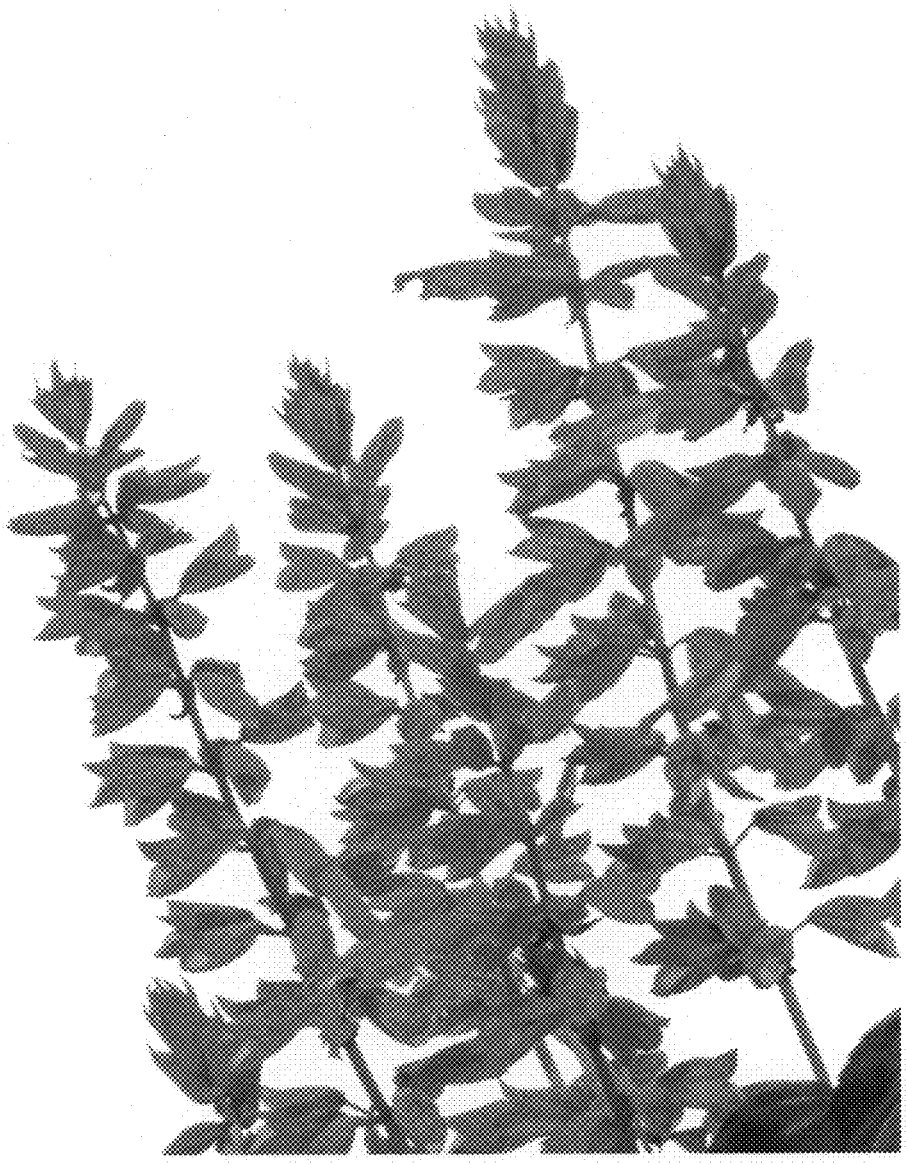

FIG. 2 illustrates in full color typical flowering spikes of 'SGRRE04-1'. Age of the plant photographed is approximately 3 months from 3 rooted cuttings.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'SGRRE04-1' plants grown in a greenhouse in Santa Paula, Calif. The growing temperature ranged from approximately 10° C. to 30° C. The greenhouse is unshaded, giving bright, normal sunlight conditions. Measurements and numerical values represent averages of typical plant types.

Botanical classification: *Salvia splendens* 'SGRRE04-1'.

PROPAGATION

Root description: Fine, densely fibrous. Colors include Green-White 157D on new growth and Orange-White 159C, Grey-Brown 199B and 199C for older roots.

PLANT

Growth habit: Upright and somewhat outwardly angled.

Pot size of plant described: 1 gallon pot.

Height: Approximately 25 cm to top of foliage. Approximately 50 cm to top of flowering plane. Measured from soil level of pot.

Plant spread: Approximately 48 cm.

Growth rate: Rapid.

Branching characteristics: Moderately well branched. Approximately 2 to 4 branches emerging from a pinch, which branch into another 2 to 4 primary lateral branches.

Length of primary lateral branches: Approximately 12 cm.

Diameter of lateral branches: Approximately 0.5 cm.

Quantity of lateral branches: About 16 to 24.

Stem:

*Color*.—Near RHS Yellow-Green 144A. Nodes lightly flushed Red 45A.

*Texture*.—Pubescent and ribbed.

Internode length: Average range 2.5 to 4.0 cm.

Age of plant described: Approximately 20 weeks from 3 rooted cuttings.

FOLIAGE

Leaf:

*Arrangement*.—Opposite.

*Quantity*.—Average range 6 to 12 fully expanded per main branch.

*Average length*.—Approximately 9.0 cm. including petiole.

*Average width*.—Approximately 3.8 cm.

*Shape of blade*.—Deltoid.

*Apex*.—Acute.

*Base*.—Truncate.

*Attachment*.—Stalked.

*Margin*.—Crenate.

*Texture of top surface*.—Matte, glabrous. Reticulate.

*Texture of bottom surface*.—Matte, glabrous, reticulate.

*Color*.—Young foliage upper side: Near RHS Green 137B. Young foliage under side: Near RHS Green 137D. Mature foliage upper side: Near RHS Green 137A. Mature foliage under side: Near RHS Green 137C.

*Venation*.—Type: Reticulate. Venation color upper side: Near RHS Yellow-Green 144B. Venation color under side: Near RHS Green 137D.

*Petiole*.—Average Length: Approximately 3.9 cm. Diameter: Approximately 0.2 cm. Color: Near Green 137A.

FOLIAGE

Leaf:

*Arrangement*.—Opposite.

*Quantity*.—Average range 6 to 12 fully expanded per main branch.

*Average length*.—Approximately 9.0 cm. including petiole.

*Average width*.—Approximately 3.8 cm.

*Shape of blade*.—Deltoid.

*Apex*.—Acute.

*Base*.—Truncate.

*Attachment*.—Stalked.

*Margin*.—Crenate.

*Texture of top surface*.—Matte, glabrous. Reticulate.

*Texture of bottom surface*.—Matte, glabrous, reticulate.

*Color*.—Young foliage upper side: Near RHS Green 137B. Young foliage under side: Near RHS Green 137D. Mature foliage upper side: Near RHS Green 137A. Mature foliage under side: Near RHS Green 137C.

*Venation*.—Type: Reticulate. Venation color upper side: Near RHS Yellow-Green 144B. Venation color under side: Near RHS Green 137D.

*Petiole*.—Average Length: Approximately 3.9 cm. Diameter: Approximately 0.2 cm. Color: Near Green 137A.

FLOWER

Natural flowering season: Flowering from early Spring until the first heavy frost.

Inflorescence type and habit: Flowers arranged in verticillasters on spikes.

Flower longevity on plant: Individual flowers last approximately 7 to 10 days on the plant. Each spike lasts approximately 4 to 6 weeks with flowers. Corolla self cleaning, calyx persistent.

Quantity of flowers: About 12 to 16 buds and 24 to 36 fully opened flowers per spike, at one time. Mature plants have approximately 20 to 30 spikes.

Spike size:

*Diameter*.—Approximately 10.0 cm.

*Height*.—Approximately 20.0 cm.

Individual flowers:

Size:

*Diameter*.—Approximately 1.0 cm.

*Length*.—Approximately 4.4 cm.

*Fragrance*.—Very faint.

Corolla:

*Petal arrangement*.—The corolla is sympetalous and typically bilabiate with 2 small, fully fused lobes forming a single upper lip and 3 larger fused lobes forming a lower lip.

*Margin*.—Entire.

*Tip shape*.—Upper lip tip obtuse, lower lip tip retuse.

*Length*.—Upper lip Approximately 1.0 cm. Lower lip Approximately 0.6 cm. Tube length Approximately 2.7 cm.

*Width*.—Upper lip: Approximately 0.4 cm, lower lip Approximately 1.0 cm. Tube width: Approximately 0.7 cm.

*Texture*.—Upper lip: Glabrous all surfaces. Lower lip: Glabrous all surfaces.

Color:

*Upper lip*.—When opening: Inner surface: Near RHS Red 44A. Outer surface: Near RHS Red 44A. Fully opened: Inner surface: Near RHS Red 42A. Outer surface: Near RHS Red 44B. Fading: Inner surface: Near RHS Red 42C. Outer surface: Near RHS Red 42B.

Color:

*Lower lip*.—When opening: Inner surface: Near RHS Red 44B. Outer surface: Near RHS Red 44B. Fully opened: Inner surface: Near RHS Red 42B. Outer surface: Near RHS Red 44C. Fading: Inner surface: Near RHS Red 42C. Outer surface: Near RHS Red 42C.

Color:

*Tube*.—When opening: Inner surface: Near RHS Red 42D. Outer surface: Near RHS Red 42B. Fully opened: Inner surface: Near RHS Red 42D. Outer surface: Near RHS Red 42B. Fading: Inner surface: Near RHS Red 42D. Outer surface: Near RHS Red 42C.

Bud: Flower bud includes immature calyx which completely surrounds immature corolla.

*Shape*.—Ovoid.

*Length*.—Approximately 1.6 cm.

*Diameter*.—Approximately 0.7 cm.

*Color*.—Near RHS Red 45A.

Calyx:

*Length*.—Approximately 2.1 cm.

*Diameter*.—Approximately 0.9 cm.

*Shape*.—Tubular.

Sepals:

*Shape*.—Quantity per flower: 3, fused to form a tube. Unfused apex.

*Length*.—Approximately 0.7 cm unfused portion.

*Width*.—Approximately 1.1 cm.

*Margin*.—Entire.

*Apex*.—Acute to short apiculate.

*Texture*.—Softly pubescent.

*Color*.—Immature: Near RHS Red 46A. Mature: Near RHS Red 46B.

Peduncle:

*Length*.—Average 4.0 cm.

*Diameter*.—0.5 cm.

*Color*.—Near RHS Red 44B.

*Orientation*.—Straight to slight outward curve, approximately 15 to 25 degree angle from center of plant.

*Strength*.—Strong.

*Texture*.—Softly pubescent, ridged.

Pedicels:

*Length*.—Average range 0.3 to 0.8 cm.

*Diameter*.—0.1 cm.

*Color*.—Near RHS Red 45A.

*Orientation*.—Straight, approximately 75 to 90 degree angle from attachment.

*Strength*.—Flexible.

*Texture*.—Pubescent.

REPRODUCTIVE ORGANS

Stamens:

*Number*.—2.

*Filament length*.—Approximately 1.7 cm.

*Filament color*.—Near RHS White N155A.

Anthers:

*Shape*.—Linear.

*Color*.—Greyed-Orange 164C.

*Length*.—About 2 mm.

*Pollen*.—Scant pollen observed, colored near Greyed-Yellow 161D.

Pistil:

*Number*.—1.

*Length*.—Approximately 3.7 cm.

*Style*.—Length: Approximately 3.4 cm. Color: Near RHS White N155C.

*Stigma*.—Shape: Forked. Color: Near RHS Red 46A. Ovary: Colored near RHS White N155C, oblong, approximately 0.3 cm long and 0.2 in diameter.

OTHER CHARACTERISTICS

Seeds and fruits: Fruit is a paper capsule, approximately 5 mm long and 3 mm wide. Colored near Grey-Orange 164C. Typically 4 seeds per pod, approximately 2 mm long and 2 mm wide. Colored near Brown 200B.

Disease/pest resistance: Neither resistance nor susceptibility to pathogens and pests common to *Salvia splendens* have been observed. The most common disease is powdery mildew (many Genus and species). Common pests include aphid and nematode.

Temperature tolerance: The new variety is a tender herbaceous perennial, tolerating temperatures within USDA zones 10 to 11.

What is claimed is:

1. A new and distinct cultivar of *Salvia* plant named 'SGRRE04-1' as herein illustrated and described.

* * * * *